US010441797B2

(12) United States Patent
Ziglio et al.

(10) Patent No.: US 10,441,797 B2
(45) Date of Patent: *Oct. 15, 2019

(54) IMPLANTABLE CARDIAC RESYNCHRONIZER WITH BIVENTRICULAR PACING AND DETECTION OF LOSS OF CAPTURE AND ANODAL STIMULATION

(71) Applicant: SORIN CRM SAS, Clamart (FR)

(72) Inventors: Filippo Ziglio, Martignano (IT); Fabrizio Renesto, Borgofranco d'Ivrea (IT)

(73) Assignee: Sorin CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/954,255

(22) Filed: Apr. 16, 2018

(65) Prior Publication Data

US 2018/0296844 A1    Oct. 18, 2018

Related U.S. Application Data

(63) Continuation of application No. 15/130,653, filed on Apr. 15, 2016, now Pat. No. 9,943,693, which is a
(Continued)

(30) Foreign Application Priority Data

May 14, 2013  (FR) ..................... 13 54330

(51) Int. Cl.
*A61N 1/36* (2006.01)
*A61N 1/37* (2006.01)
(Continued)

(52) U.S. Cl.
CPC ......... *A61N 1/3712* (2013.01); *A61N 1/3627* (2013.01); *A61N 1/3682* (2013.01);
(Continued)

(58) Field of Classification Search
CPC .... A61N 1/00; A61N 1/36185; A61N 1/3627; A61N 1/36542; A61N 1/368;
(Continued)

(56) References Cited

U.S. PATENT DOCUMENTS 6,687,545 B1    2/2004  Lu
9,943,693 B2 *  4/2018  Ziglio .................. A61N 1/3714
(Continued)

FOREIGN PATENT DOCUMENTS

EP    0 515 319 A1    11/1992
EP    1 108 446 A1    6/2001
(Continued)

OTHER PUBLICATIONS

Search Report for French Patent Application No. FR 1354330, dated Oct. 11, 2013, 2 pages.

*Primary Examiner* — Jon Eric C Morales
(74) *Attorney, Agent, or Firm* — Foley & Lardner LLP

(57) ABSTRACT

A medical device for stimulating the heart using biventricular stimulation. The device includes a sensor for detecting an endocardial acceleration parameter and a processing circuit configured to receive the endocardial acceleration parameter. The device further includes stimulation electronics coupled to the processing circuit. The processing circuit is configured to use the EA parameter to evaluate the biventricular stimulation. The evaluation includes comparing the value of the EA parameter in biventricular mode to the value of the EA parameter in left only mode or right only mode, and using the comparison and an assessment of the variability of the EA parameter as a function of the AVD in the left or right mode to distinguish between cases comprising: (a) normal operation, (b) a loss of RV or LV capture, (c) possible anodal stimulation. The processing circuit is further
(Continued)

configured to conduct at least one update to operational parameters of the device based on the determined case.

20 Claims, 4 Drawing Sheets

Related U.S. Application Data continuation of application No. 14/277,552, filed on May 14, 2014, now Pat. No. 9,314,636.

(51) Int. Cl.
    *A61N 1/362*     (2006.01)
    *A61N 1/368*     (2006.01)
    *A61N 1/365*     (2006.01)

(52) U.S. Cl.
    CPC ......... *A61N 1/3684* (2013.01); *A61N 1/3686* (2013.01); *A61N 1/36578* (2013.01); *A61N 1/3714* (2013.01)

(58) Field of Classification Search
    CPC .............. A61N 1/3686; A61N 1/36578; A61N 1/3682; A61N 1/3684; A61N 1/3688
    USPC .............................................................. 607/9
    See application file for complete search history.

(56) References Cited

U.S. PATENT DOCUMENTS

| | | |
|---|---|---|
| 2006/0293715 A1 | 12/2006 | Plicchi et al. |
| 2009/0306732 A1 | 12/2009 | Rosenberg et al. |
| 2010/0125309 A1 | 5/2010 | Casset |
| 2010/0262204 A1 | 10/2010 | McCabe et al. |
| 2011/0093027 A1 | 4/2011 | Renesto et al. |
| 2012/0022607 A1 | 1/2012 | Giorgis et al. |

FOREIGN PATENT DOCUMENTS

| | | |
|---|---|---|
| EP | 1 249 254 A2 | 10/2002 |
| EP | 1 736 203 A1 | 12/2006 |
| EP | 2 092 885 A1 | 8/2009 |
| EP | 2 495 013 | 9/2012 |

\* cited by examiner

IMPLANTABLE CARDIAC RESYNCHRONIZER WITH BIVENTRICULAR PACING AND DETECTION OF LOSS OF CAPTURE AND ANODAL STIMULATION

CROSS-REFERENCE TO RELATED APPLICATION

This application is a continuation of U.S. application Ser. No. 15/130,653, filed Apr. 15, 2016, which is a continuation of U.S. application Ser. No. 14/277,552, filed May 14, 2014, which claims the benefit of and priority to French Patent Application No. 1354330, filed May 14, 2013, all of which are hereby incorporated by reference in their entirety.

BACKGROUND

The invention relates to "active implantable medical devices" as defined by Directive 90/385/EEC of 20 Jun. 1990 of the Council of the European Communities.

It relates more particularly to implantable devices to continuously monitor the heart rhythm and deliver if necessary electrical pulses to the heart to ensure joint and permanent stimulation of the left and right ventricles to resynchronize them, a technique called "CRT" (Cardiac Resynchronization Therapy) or "BVP" (Bi-Ventricular Pacing).

A CRT pacemaker is disclosed, for example, in EP 1108446 A1 (ELA Medical), which describes a device for applying, between the respective moments of stimulation of the left and right ventricles, a variable delay called "interventricular delay" (DVV or VVD), adjusted to resynchronize the contraction of the ventricles with fine optimization of the patient's hemodynamic status. Indeed, a simultaneous stimulation of both ventricles is not always optimal. It is not always optimal because it does not necessarily result in a synchronous contraction of both ventricles. Conduction delays in the myocardium that are not the same in the right and in the left cavities can be present, and can depend on multiple factors. Furthermore, depending on the location of the left ventricular lead, whether it is introduced into the coronary sinus or it is an epicardial lead.

In some cases it is desirable to establish a delay between the two stimuli, and to adjust this delay to resynchronize the contraction of the ventricles and thus ensure a fine optimization of hemodynamics. The VVD may be zero, positive (the left ventricle is stimulated after the right ventricle) or negative (the right ventricle is stimulated after the left ventricle).

CRT devices can include a classic "dual chamber" mode wherein the device monitors ventricular activity after a spontaneous (detection of a P wave of atrial depolarization) or stimulated (application of an atrial stimulation A pulse) atrial event. At the same time, the device starts counting a delay called "atrioventricular delay" (DAV or AVD) such that if no spontaneous ventricular activity (R wave) has been detected at the end of this period, then the device initiates stimulation in this ventricle (V pulse application). Often dramatic results have been observed in clinical studies for patients with heart failure not improved by conventional treatments, since the parameters of the CRT therapy are accurately adjusted according to the patient and the nature of his myocardial contraction condition (e.g., such as dilatation of the heart chambers, low ejection fraction, and excessive lengthening of the QRS complex—whether this disorder is spontaneous or induced by traditional stimulation).

Various clinical studies have shown that the endocardial acceleration (hereinafter "EA") is a parameter that relatively precisely and in real time reflects the phenomena related to movements of the heart chamber. An EA signal can provides comprehensive information on cardiac mechanics, both for normal operation and for a deficient functioning. The endocardial acceleration is measured, for example, by an accelerometer integrated into an endocardial lead, for example as described in EP 0515319 A1 (Sorin Biomedica Cardio SpA).

EP 1736203 A1 (ELA Medical) describes a technique for evaluating in a simple, rapid, automated and accurate method the impact of various parameters of the CRT stimulation, including AVD and VVD delays, by running an AVD scan in a given stimulation configuration (that is to say, with a given DVV), to plot a characteristic giving the value of the peak of endocardial acceleration PEA versus the AVD, so as to select the optimal pair {AVD, VVD}. The intent is to determine, at the time of implantation or later, the optimal pacing configuration that optimizes the patient's hemodynamic status.

However, effective therapy involves the delivery of appropriate stimulation pulses that provide ventricular capture (that is to say, the applied pulse has induced, both in the right and left cavities, a depolarization of the cavity), as it is an essential condition for the resynchronization. To verify the presence of this capture, devices are provided with "capture test" methods for determining whether a stimulation has been effective or not for one or both of the ventricles. These methods operate by search and analysis of the "evoked wave" (the depolarization wave induced by stimulation of the concerned cavity).

The capture test can provide for an assessment of the "triggering threshold." The triggering threshold is the minimum pacing energy required to cause depolarization of the ventricle (the thresholds may be different between the right site and the left site). It may be desirable to adjust the amplitude and/or the width of the stimulation pulse in order to guarantee that any stimulation cause an evoked wave and to ensure the energy delivered will not be excessive (e.g., so as not to affect too much the battery lifespan of the implant due to unnecessarily high energy consumption). The capture test can be performed at regular intervals, and can performed on a continuous, cycle-to-cycle basis.

A recent trend in biventricular stimulation is the multiplication of the "stimulation vectors." This technique can involve applying the stimulation between different pairs of electrodes selected to optimize the applied therapy, each of the right and left leads being provided with a plurality of selectively switchable electrodes. Conventional "bipolar" stimulation is provided between a tip electrode (tip) and an annular electrode (ring) located near the right lead, or even on the left lead.

Some CRT devices also include an alternative called "pseudo-bipolar" configuration, wherein the stimulation of the left ventricle is caused by the electrode end (tip) of the left ventricular lead and the annular electrode (ring) or a defibrillation coil of the right ventricular lead. This "pseudo-bipolar" stimulation configuration of the left ventricle may provide benefits including reducing pacing thresholds and reducing the risk of stimulation of the phrenic nerve.

However, the use of multiple and different stimulation vectors can cause fluctuations of the associated pacing thresholds and create a corresponding increased risk of loss of capture. The use of multiple and different stimulation vectors can also create occurrence of a phenomenon called "anodal stimulation." Anodal stimulation is characterized by a reversal of the anode and cathode during stimulation, with the result that the stimulation is not normally delivered (i.e. solely at the cathode) and the depolarization wave induced by this inverse stimulation may not be the desired one, and unexpected results can occur.

One example in the case of a "pseudo-bipolar" stimulation is as follows. Normally, the stimulation would occur between an electrode of the left lead (as cathode) and an electrode of the right lead (as anode) to stimulate the left ventricle, and the evoked wave is normally generated at the cathode (on the left ventricular site). But, in some situations, the depolarization wave of the left ventricle is not created only at the cathode (and therefore in the left ventricle), but also at the anode (and hence in the right ventricle). Therefore, the pulse to contract the left ventricle will also generate a right depolarization ("anodal stimulation" phenomenon). The consequence is that the depolarization wave corresponding to the pulse applied to the left cavity will produce a depolarization in the right ventricle at the same time. This can lead to loss of the benefit of an anticipated left stimulation during resynchronization therapy.

The risk of occurrence of anodal stimulation may be increased by the use of dedicated bipolar leads using a relatively small surface area of electrode as the anode. In pseudo-bipolar pacing, such an electrode can generate a high current density in its immediate environment, thus increasing the risk of triggering a sudden unexpected depolarization of the myocardium.

If anodal stimulation is not identified and corrected, this may remove the beneficial effects of a programmed VVD, and lead to sub-optimal resynchronization, characterized for example, by a concomitant contraction of both ventricles (a loss of VVD). This phenomenon is not rare in patients undergoing biventricular pacing. If it is detected, some devices may take reactive measures, such as changing the pacing configuration by switching to another stimulation vector not resulting in anodal stimulation (e.g. a pure bipolar vector, a unipolar vector or another interventricular vector by selection of other electrodes of the right and/or left leads).

Certain conditions favor the occurrence of a phenomenon of anodal stimulation. Such conditions may include: relatively high stimulation amplitudes, close to the stimulation threshold; and an "intercavity stimulation vector" or "pseudo-bipolar" configuration in which a stimulation is applied in a given cavity (e.g. the left ventricle) with the lead located on an anode in the opposite cavity (for example an electrode of a right ventricular lead).

These conditions can arise during the execution of a capture test, and thus repeatedly during a critical phase of the evaluation of the effectiveness of the stimulation. Indeed, the capture threshold test begins with high stimulation energy. This risk diminishes gradually with the reduction of the stimulation amplitude, but the test algorithm may have already been confused by anodal stimulation (that has not been identified as such) by a loss of capture. Such confusion can lead to misclassification of successive cycles of tests between capturing cycles and non-capturing cycles.

U.S. Pat. No. 6,687,545 B1 discloses a device for identification, during a capture test, of such a situation of anodal stimulation.

SUMMARY

The object of the disclosure is to propose a new analysis technique that increases the effectiveness of biventricular pacing, accurately detects a loss of capture in the right and/or in the left cavities, and also accurately detects the appearance of a phenomenon of anodal stimulation.

The object of the invention is to disclose a technique for automatic verification of the effectiveness of biventricular pacing. The technique uses endocardial acceleration (EA) signals collected during the periodically executed automatic adjustment procedures of the AVD and VVD. If the analysis of these EA signals or of parameters derived of these signals, for different stimulation configurations, reveals a lack of effectiveness of CRT therapy, then the device will trigger an alert to update the capture thresholds and/or modify the stimulation configuration.

The invention discloses an active implantable medical device for cardiac resynchronization by biventricular pacing. Some embodiments include a processing circuit for detecting atrial and ventricular events, a circuit for stimulation of the right and left ventricles, circuitry for stimulation of an AVD (e.g., counted from the detection of a spontaneous or paced atrial event and at the end of which a right ventricular pacing is applied in the absence of a sensed spontaneous ventricular event), the processing circuit may be configured to apply a VVD between the respective instants of stimulation of the right and left ventricles. The processing circuit may further be configured to cause the device to selectively operate in: a right mode wherein only the right ventricle is paced; a left mode wherein only the left ventricle is stimulated; or in a biventricular mode wherein both ventricles are stimulated together with or without application of a VVD.

The device may further include a sensor for delivering an EA endocardial acceleration signal. The processing circuit may extract, from the EA signal, at least one predetermined EA parameter. The processing circuit may be configured to conduct evaluation during the biventricular stimulation. The evaluation may include comparing the values of the characteristic EA parameter obtained respectively in biventricular mode and in left mode and to determine whether the difference between these values exceeds a first predetermined threshold. The evaluation may include comparing the values of the characteristic EA parameter obtained respectively in biventricular mode and in right mode to determine if the difference between these values exceeds a second predetermined threshold. The evaluation may further include determining if the variation of the characteristic EA parameter for different AVD in left mode exceeds a third given threshold. The evaluation may further include determining if the variation of the characteristic EA parameter for different AVD in right mode exceeds a fourth given threshold. The evaluation may further include comparing the values of the characteristic EA parameter obtained in biventricular mode with a negative or positive VVD and determining if the difference between these values exceeds a fifth predetermined threshold. The method also includes determining, in response to the previous thresholds analyses, the occurrence of a possible loss of capture in the left or right cavities, or the presence of an anodal stimulation phenomenon.

The device may conduct a preliminary testing of a plurality of different stimulation configurations with different DVV for a plurality of AVD. The device may conduct a prior (i.e., initial) selection of the characteristic EA parameter among several possible predetermined characteristic EA parameters, based on the results produced by the prior test methods of a plurality of configurations.

The evaluation including the second threshold may be conducted in response to a determination that the difference between the values of the characteristic EA parameter obtained in biventricular mode and in left mode exceeds the first threshold. The next evaluation step may be initiated if the second method determines that the difference between the values of the characteristic EA parameter obtained in biventricular mode and in right mode does not exceed the second threshold. The occurrence of a loss of capture in the left cavity may be determined if the evaluation determines that the variation of the characteristic EA parameter for different AVD in left mode does not exceed the third threshold.

The fourth threshold check may be implemented if the first evaluation determines that the difference between the values of the characteristic EA parameter obtained in biventricular mode and in left mode does not exceed the first threshold. The occurrence of a loss of capture in the right cavities may be determined if the evaluation determines that the variation of the characteristic EA parameter for different AVD in right mode does not exceed the fourth threshold. The evaluation involving the fifth threshold may be conducted in response to a determination that the variation of the characteristic EA parameter for different AVD in right mode exceeds the fourth threshold. The presence of an anodal stimulation phenomenon may be determined if it is determined that the variation of the characteristic EA parameter for different VVD with stimulation of the left ventricle first does not exceed the fifth threshold.

The device may also be configured to update the stimulation energy of the left or right ventricle. The stimulation energy adjustment may be conducted in response to the determination of the occurrence of a loss of capture respectively in the left or in the right cavities. The device may further include updating the stimulation energy of the left ventricle or for modification of the configuration of the pacing electrodes. This update may be implemented in response to the determination of the presence of an anodal stimulation phenomenon.

The device may be configured to apply an atrioventricular delay AVD and an interventricular delay VVD. The device can selectively operate in right only mode, left only mode or biventricular mode, and extract a characteristic parameter of the signal from an EA endocardial acceleration sensor. To evaluate the effectiveness of biventricular pacing, the device can compare the values of the EA parameter in biventricular mode and in left only mode, or right only mode, and can determine if the difference exceeds a given threshold. The device can assess the variability of the EA parameter as a function of the AVD in left or right mode. The device then compares the values of the EA parameter in biventricular mode, with a negative or positive VVD and determines if the difference (between the EA parameter in the biventricular mode with the EA parameter in the negative or positive VVD mode) exceeds a given threshold. In response, the device indicates the occurrence of a possible loss of capture on the left or right cavities, or the presence of an anodal stimulation phenomenon.

DETAILED DESCRIPTION

The invention may be implemented by configuring or reprogramming the controlling software for a stimulator such as a cardiac pacemaker, a resynchronizer or defibrillator. The invention may notably be applied to implantable devices, such as that of the Reply and Paradym families, manufactured and commercialized by Sorin CRM, Clamart, France. Embodiments of the device may include programmable microprocessor circuitry configured to receive, format and process electrical signals collected by implantable electrodes, and deliver stimulation pulses to these electrodes.

The methods of the invention may be implemented by software (e.g., executable program code stored in memory), automatically (e.g., repeatedly) executed by a microcontroller or a digital signal processor.

Figure 1:
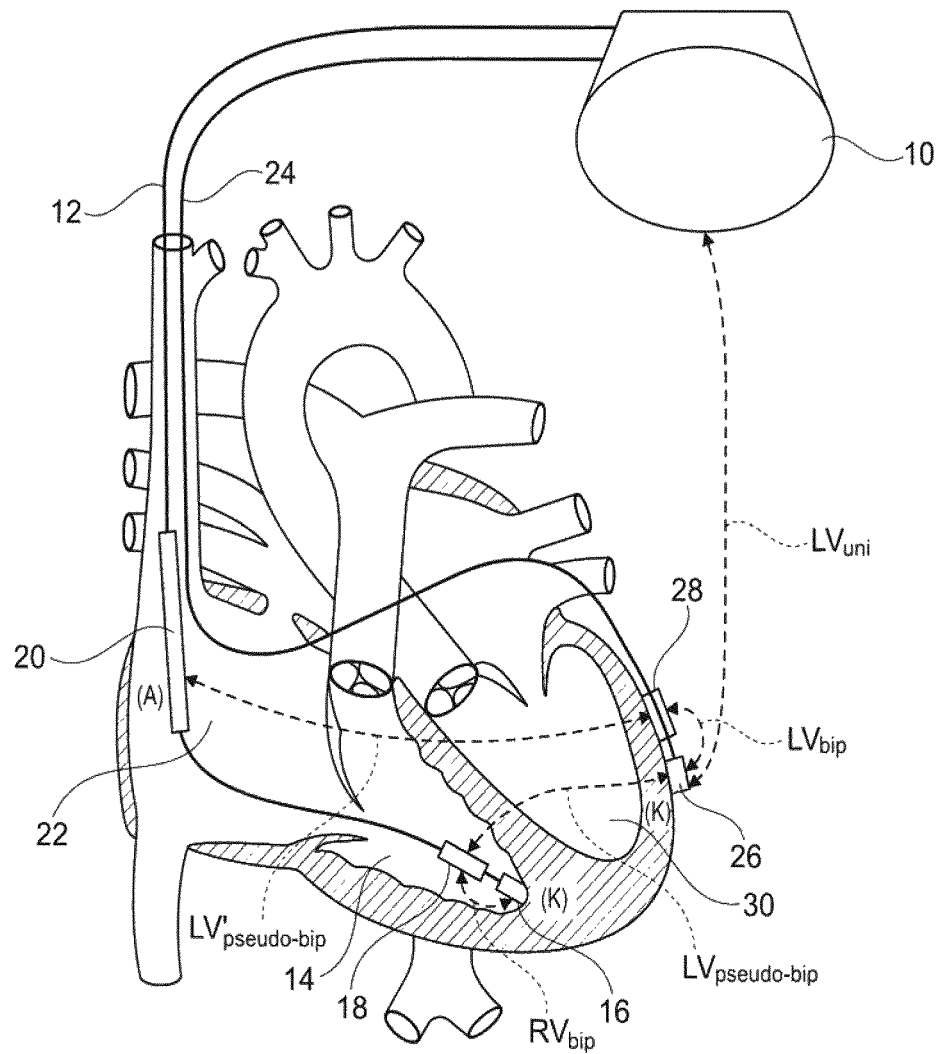
FIG. 1 is an overall view showing the implantation of pacing leads of the right and left ventricles, with the different stimulation vectors that can be used as part of a biventricular pacing.

FIG. 1 illustrates a device for biventricular pacing, according to an exemplary embodiment. The pulse generator 10 is associated with a first lead 12 located in the right ventricle 14. The head of the lead includes two electrodes. The electrodes can include a distal electrode (tip) 16 and a proximal electrode (ring) 18. The lead can also be provided with a coil 20 forming an electrode for defibrillation and/or for collecting an endocardial signal (EGM signal) in the right atrium 22.

The right ventricle (or RV) is usually stimulated by application of pulses between the electrodes of ends 16 and 18 of the lead 12. This configuration for stimulation of the right ventricle is designated in FIG. 1 as "$RV_{bip}$".

The left ventricle (or LV), can be stimulated using a variety of different configurations. Each configuration may be selected by the controlled appropriate switching of the electrodes in the generator 10. Configurations of the left ventricle may include:

an unipolar configuration $LV_{uni}$, between either of electrodes 26 or 28, on the one hand, and the housing (can) of the generator 10;

a bipolar configuration $LV_{bip}$ between the two end electrodes 26 and 28 of the lead 24;

a first "pseudo-bipolar" configuration $LV_{pseudo-bip}$ between, on one hand, one of the end electrodes of the left lead 24, for example the distal electrode 26 and, on the other hand, one of the end electrodes of the right ventricular lead 12, e.g. the right proximal electrode 18; and a second pseudo-bipolar configuration $LV_{pseudo-bip}$, between, on the one hand, one of the end electrodes of the left lead 24, for example the proximal electrode 28 and, on the other hand, the coil 20 of the right lead 12.

The electrical pulses are applied by the generator between the different pairs of electrodes, so as to locally induce depolarization of the electrode forming cathode, which is the distal electrode 16 or 26 in the case of a bipolar or unipolar pacing; the anode being, according to the case, the metal housing or the generator 10 or the proximal electrode 18 or 28.

In the case of a pseudo-bipolar pacing of the left ventricle, the cathode is the electrode 26 or 28 positioned against the left ventricle, the anode being the electrode 18 or 20 of the right lead, respectively, used only to define a current return to the generator.

As discussed above, in some situations, the depolarization wave of the left ventricle is not created only at the cathode (and therefore in the left ventricle), but also at the anode (and thus at the right ventricle). In other words, the pulse to contract the left ventricle will also generate a depolarization in the right cavity (phenomenon of "anodal stimulation"). The phenomenon of anodal stimulation results in the depolarization wave corresponding to the pulse applied to the left cavity will produce at the same time a depolarization in the right ventricle, leading to the loss of an anticipated left stimulation during resynchronization therapy.

The risk of occurrence of anodal stimulation is relatively high during a capture threshold test, which may begin with a high stimulation energy. The risk then diminishes gradually as the amplitude of stimulation reduces. However, the capture test algorithm may have some incorrect information if it wrongly interprets the disappearance of the anodal stimulation (that it did not identify as such) by a loss of capture. Bad information during capture tests can lead to misclassification of the successive cycles of test cycles between capturing and non-capturing cycles.

The technique of the invention overcomes this difficulty, by a new technique for analyzing the effectiveness of biventricular pacing allowing identification of not only a loss of capture in the right and/or the left cavities, but above all, the appearance of a phenomenon of anodal stimulation.

Figure 2:
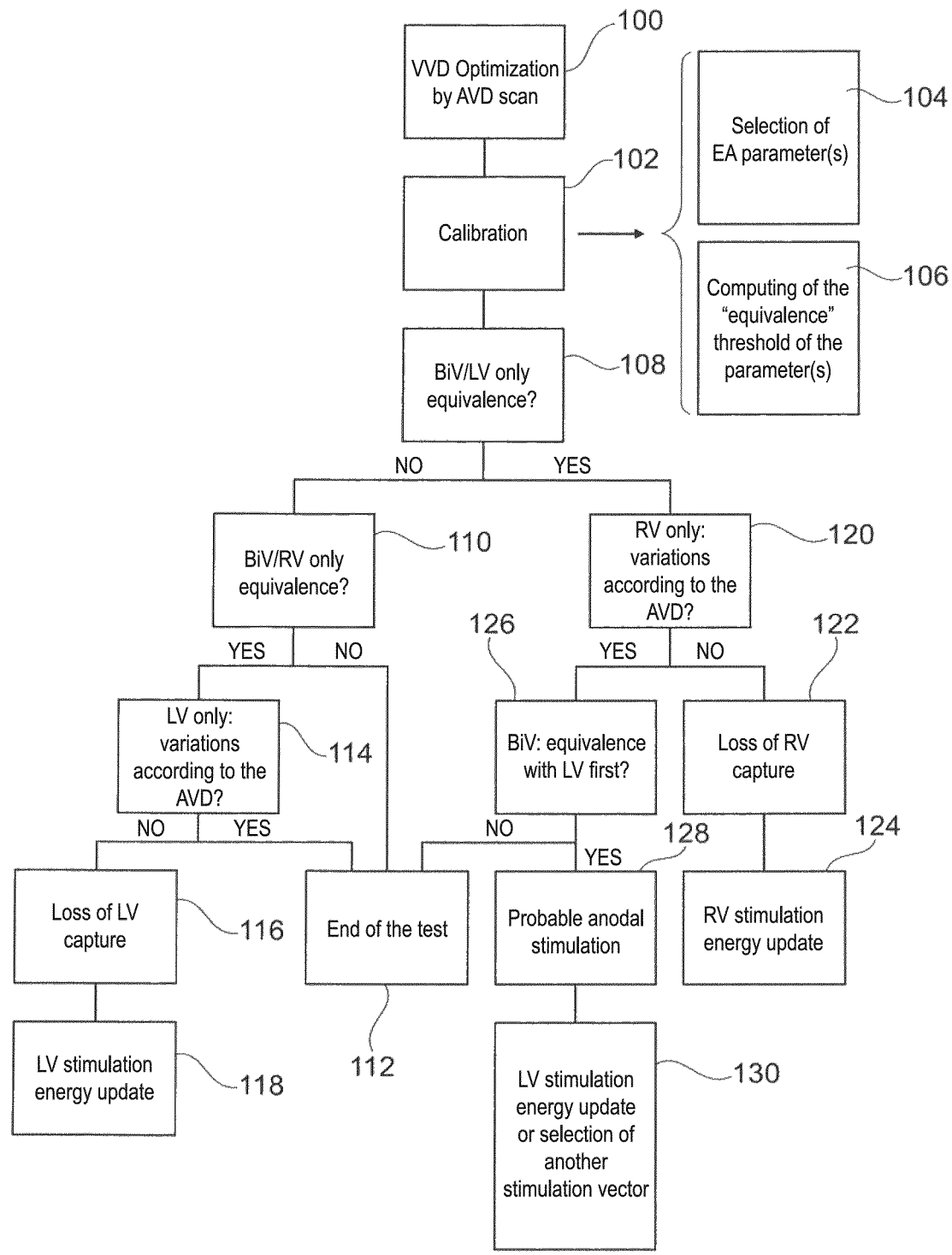
FIG. 2 is a flow chart illustrating the varying method steps of the analysis and optimization technique for/of the biventricular stimulation, according to an exemplary embodiment.
Figure 3:
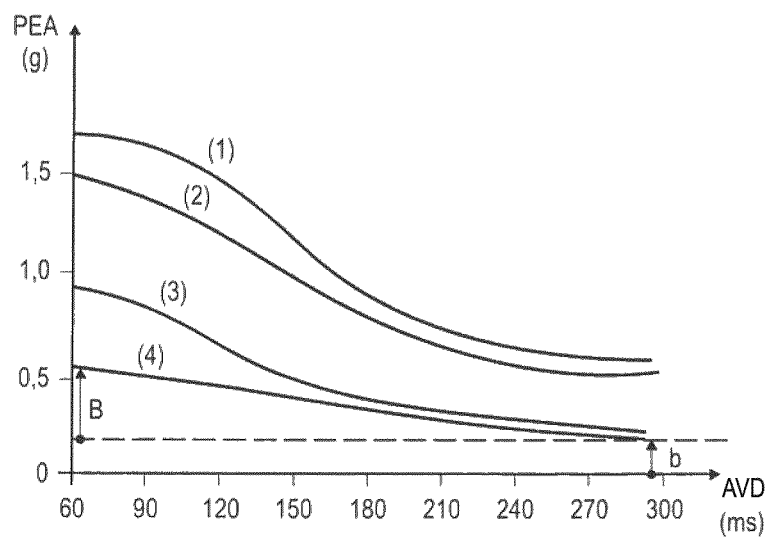
FIG. 3 illustrates a family of characteristics of variation of the amplitude of the EA peak as a function of the AVD, for different VVD values.

FIG. 2 is a block diagram illustrating the different steps of the analysis and optimization of biventricular stimulation according to the invention technique. The first step (block 100) is running a conventional optimization of AVD and VVD by scanning the AVD for a given VVD, then performing analysis of the variations of the EA signal resulting from these changes of the AVD. The principle of this evaluation is illustrated in FIG. 3, which plots a characteristic defined by the variation of the amplitude of the first peak of endocardial acceleration (PEA) according to the AVD, for different possible values of VVD (values corresponding to different curves (1) to (4) of the family of illustrated curves). In the case of appropriate CRT stimulation, the curve takes a characteristic sigmoid shape, wherein the AVD varies between the two extremes. This can be interpreted by the fact that the decrease in amplitude of the PEA with an increasing AVD is mainly determined by:

The "contractility reserve" of the myocardium, corresponding to the level of the base line b (the lower limit value of the PEA for the longest AVD); and The "noise" generated by the heart valves, especially the mitral valve, which determines the amplitude level rise above this baseline for the shortest AVD (B in FIG. 3).

This scan may be performed for at least three different VVD, each time for at least six AVD values (according to an exemplary embodiment), selected to be shorter than the spontaneous AV conduction (PR/AR interval) of the patient.

The next step (block 102) is a step unique to the invention, called "calibration", which aims to:

Determine at least one EA parameter that may appropriately reflect the differences between multiple tested pacing configurations (block 104), and To determine for the EA parameter(s) thus selected an "equivalence" threshold (block 106), based on the intrinsic variation of the EA parameter, which will allow for deciding whether two modes of stimulation can be considered as substantially producing the same effect (they are described as "equivalent") or not.

EP 2495013A1 (Sorin CRM) and EP 2092885 A1 (ELA Medical) illustrate the method to analyze an EA signal collected by an endocardial acceleration sensor, and derive a number of representative parameters ("EA parameters"). The two documents cited above can be referred to for more details on the method of determining these EA parameters, as well as other characteristics of the EA1 and EA2 components. Some representative EA parameters include:

The value of the peak-to-peak amplitude of the EA1 component (hereinafter simply referred to as "PEA");

The time of occurrence of the beginning of the EA1 component, represented by the time interval between i) a temporal marker of the start of a cardiac cycle and ii) the crossing of an energy envelope threshold of the EA1 component;

The time interval between i) the crossing of the energy envelope threshold of the EA1 component and ii) the moment of the peak of the energy envelope of the EA1 component;

The length of the systole, represented by the time interval between the start of the EA1 component and the start of the EA2 component; and/or Composite EA parameters combining the previous ones.

Step 104 may include selecting, among the various possible EA parameters, an EA parameter (or possibly several of these EA parameters) to assess the best the effect of a change in the configuration and in the stimulation mode, in order to detect the possible presence of anodal stimulation and/or of a loss of left or right ventricular capture. This EA parameter is selected by an operator.

The various possible stimulation modes that will be tested on the basis of the thus selected EA parameter are:

Stimulation of the left ventricle only (LV), hereinafter "L Mode" or "LV only";

Stimulation of the right ventricle only (RV), hereinafter "R mode" or "RV only";

Concomitant stimulation of both ventricles, hereinafter "biventricular mode" or "BiV" with application of a zero, positive or negative VVD.

Step 106 may include calculating the "equivalence threshold" of the selected EA parameter is to define a threshold for distinguishing between two different hemodynamic situations, in a method not correlated with the intrinsic variability of the EA parameter.

If we take as an example of an EA parameter, the PEA (the average value of the peak-to-peak of the first EA peak for the different applied AVD), we may define an equivalence indicator by the percentage of the mean square error (RMSE) between two stimulation conditions with different VVD, VVD1 and VVD2:

$$RMSE = 100 \times \sqrt{\frac{\sum_{i=1}^{n} \left(\frac{(\Delta_i)}{P1i}\right)^2}{n}}$$

n being the number of tested AVD for each condition of stimulation (for VVD1 and for VVD2), and $$\Delta_i = (P1_i - P2_i),$$

P1$_i$ and P2$_i$ being the values of the considered EA parameter (PEA here) measured for the i$^{th}$ AVD, respectively for VVD=VVD1 and for VVD=VVD2.

Figure 4:
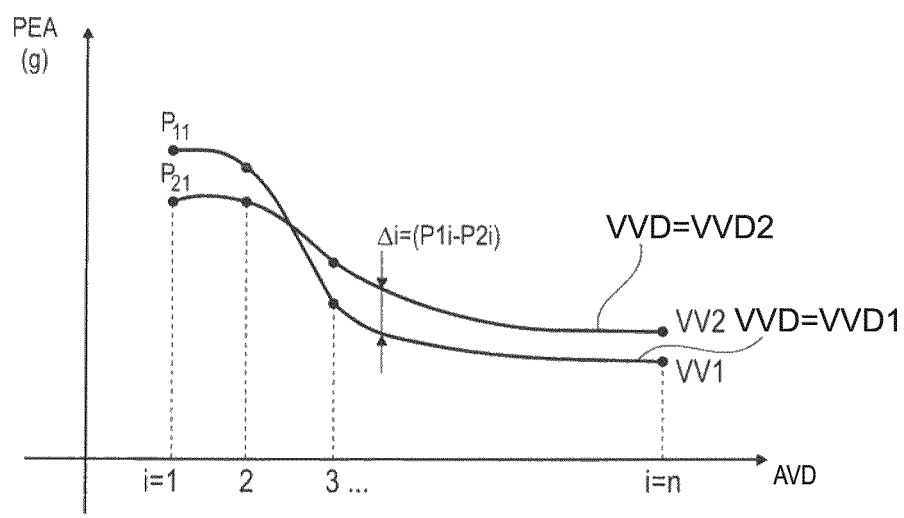
FIG. 4 illustrates two characteristics of the variation of the EA peak amplitude as a function of the AVD, compared to determine if they are equivalent or not, depending on their inherent variability.

FIG. 4 shows an example of variation between these parameters. It may be decided that the value of RMSE between VVD1 and VVD2 is less than a predefined threshold (e.g. 10%, but this value may also depend on the intrinsic variability of the EA parameter over consecutive cycles keeping the same VVD). If this is true, then the two stimulation configurations will be considered as "equivalent". This equivalence indicator will also be used to assess this same "equivalence" between different stimulation modes (LV only, RV only or BiV).

Once the calibration phase (block 102) is completed, the evaluation of the effectiveness of the biventricular stimulation begins with a test of equivalence between a BiV pacing mode and a LV only pacing mode (block 108). A negative response to this test corresponds to a normal case, to the extent that the biventricular stimulation reveals a different hemodynamic status (therefore not equivalent) compared to a stimulation of the left ventricle only.

The algorithm then tests the equivalence between the BiV and RV only modes (block 110). A negative response corresponds to the typical, normal, expected case wherein the bi-ventricular pacing is normally more effective than the VD only pacing mode. The analysis then ends by returning a result indicating that biventricular pacing is consistent and efficient (block 112).

If, however, equivalence is found between BiV and RV only pacing modes (block 110), this means that biventricular pacing brought nothing compared to stimulation of the right ventricle only.

The algorithm then analyzes (block 114) in LV only mode, the variation of the EA parameter as a function of AVD. If the variation of the AVD produces no effect, this can mean that there is a loss of capture in the left ventricle (block 116). In response to such a determination it may be necessary to trigger a capture test to reassess the stimulation energy of the left ventricle and adjust it to a higher level (block 118).

If, however, a variation of the AVD induces an effective variation of the EA parameter, there is no longer a suspected loss of capture and the stimulation should be recognized consistent (block 112).

If, when comparing BiV and LV only pacing modes (block 108), these two modes have been recognized as equivalent, this situation is abnormal because it means that hemodynamically biventricular pacing brought nothing compared to a stimulation of the left ventricle only. The cause may be a right loss of capture or anodal stimulation, causes that should be discriminated because remedies will not be the same in each situation.

This situation of probable anodal stimulation (block 128) appears in the following context:
Programming a pseudo-bipolar stimulation vector (LV$_{pseudo-bip}$ or LV'$_{pseudo-bip}$ on FIG. 1);
Presence of a variability of the EA parameter for different AVD in RV only mode (test block 120); and
Equivalence of values of the EA parameter between a pure biventricular stimulation situation (VVD=0) and one or more stimulation configurations of the LR type, that is to say with a first stimulation in the left cavity (test of block 126).

The algorithm then tests the effect of a variation of the AVD on the EA parameter in RV only pacing mode (block 120, similar to block 114, for but pacing in the right cavity). The lack of change after the test reveals a loss of capture in the right cavity (block 122), which should be remedied by triggering a capture test and update of the stimulation energy of the right ventricle (block 124). If, however, a change in the AVD actually induces a variation of the EA parameter (block 120), the presence of this variability suggests the occurrence of a phenomenon of anodal stimulation.

To remove this doubt, the test continues by evaluating (block 126) the equivalence between configurations with different VVD, but wherein left side stimulation precedes the right side stimulation (configuration "left first" or "LR"):
If an equivalence is found between these configurations, this may mean that, hemodynamically, the variation of the VVD produces no results between the first stimulation in the left cavity and the second stimulation in the right cavity, typical situation of the presence of anodal stimulation (block 128). It is therefore necessary to update the stimulation energy of the left ventricle, or to change the polarity of the stimulation of the left ventricle by a different selection of electrodes, so as to define another stimulation vector (block 130);
If, instead, changing the VVD configuration in a "LR" configuration induces changes in the EA parameter (non-equivalence), there is no anodal stimulation (block 112) and a change in the stimulation energy or in the stimulation vector will not be required.

Figure 5:
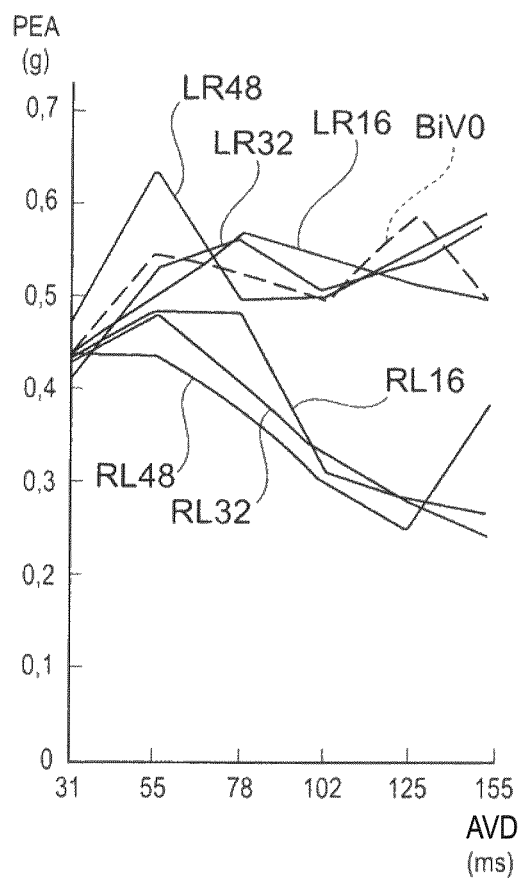
FIG. 5 illustrates an example of measurement results of the amplitude of the PEA according to the AVD for different values of VVD, especially in the presence of a phenomenon of anodal stimulation.

FIG. 5 illustrates an example of measurement results of the amplitude of the PEA according to the AVD for different values of VVD, especially in the presence of an anodal stimulation phenomenon. These results are presented as a histogram in FIG. 6, with for different VVD the average values of PEA are classified according to the respective VVD.

In these figures the "LRnn" indications correspond to stimulation of the left ventricle first, followed by that of the right ventricle, the numerical value nn indicating the applied VVD (e.g. 16, 32 and 48 ms). The "RLnn" indications correspond to the reverse situation, wherein the right ventricle is paced first. The reference "BiV0" indicates biventricular stimulation with VVD equal to zero, that is to say, applied simultaneously to the two ventricles.

Figure 6:
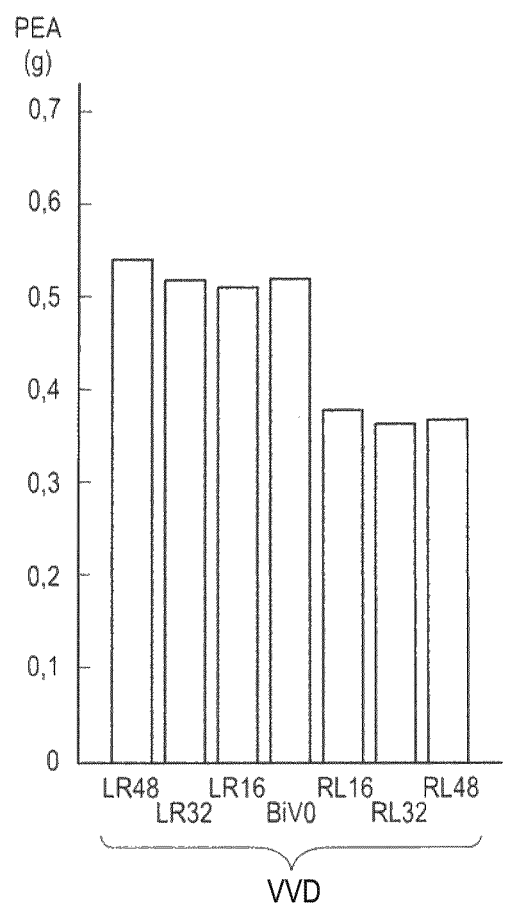
FIG. 6 is an illustration as a histogram of the results of FIG. 5, giving for various VVD the average of the PEA values classified according to the respective DVV.

The illustrated example corresponds to a clinical case wherein an anodal stimulation is present during the left ventricular stimulation. As can be seen in the histogram of FIG. 6, the values of the EA parameter associated with configurations with a left ventricular stimulation first (LR configurations) are all equivalent to those measured in pure biventricular configuration BiV0, indicating the ineffectiveness of applying a VVD, regardless of the value thereof. By contrast, for a stimulation of the right ventricle first (in the example, RL16, RL32 and RL48 configurations) a significant difference appears compared to biventricular pacing pure BiV0, revealing the effectiveness of the application of the VVD. Moreover, we observe on the characteristics PEA/AVD in FIG. 5 that the characteristics RL16, RL32 and RL48 are very different from the LR16, LR32 and LR48 configurations.

What is claimed is:
1. An active implantable medical device that provides cardiac resynchronization by biventricular pacing, comprising:
a memory storing a plurality of executable instructions; and
a processor configured to execute the instructions to:
selectively operate a stimulation in a first mode and a second mode, the first mode comprising a right only mode wherein a right ventricle is stimulated and a left ventricle is not stimulated or a left only mode wherein the left ventricle is stimulated and the right ventricle is not stimulated, the second mode comprising a biventricular mode in which both the left ventricle and the right ventricle are stimulated;

receive, from an endocardial acceleration sensor, an endocardial acceleration (EA) signal in each of the first mode and the second mode;

extract, from the EA signal, an EA parameter in each of the first mode and the second mode;

use the extracted EA parameters to evaluate the stimulation in the second mode, the evaluation comprising comparing values of the EA parameter in the second mode to the values of the EA parameter in the first mode to distinguish between: (a) normal operation, (b) a loss of a right ventricular capture or a left ventricular capture, and (c) possible anodal stimulation.

2. The device of claim 1, further comprising:
a sensor configured to detect atrial and ventricular events; and
at least one electrode configured to stimulate the right and left ventricles.

3. The device of claim 1, wherein the processor is further configured to execute the instructions to conduct at least one update to operational parameters of the device based on the determined case.

4. The device of claim 1, wherein the processor is further configured to determine whether a difference between the values of the EA parameter in first mode and the second mode exceeds a first predetermined threshold.

5. The device of claim 4, wherein the processor is further configured to determine whether a difference between the values of the EA parameter in the first mode and the second mode exceeds a second predetermined threshold.

6. The device of claim 5, wherein the processor is further configured to execute the instructions to:
apply an atrioventricular delay (AVD) counted from a detection of a spontaneous or paced atrial event;
apply a right ventricular pacing at an end of the AVD in absence of a detected spontaneous ventricular event;
apply an intreventricular delay (VVD) between respective times of stimulation of the left ventricle and the right ventricle; and
use the comparison of the values of the EA parameter in the second mode to the values of the EA parameter in the first mode to assess a variability of the EA parameter as a function of the AVD in the first mode to distinguish between the normal operation, the loss of the right ventricular capture or the left ventricular capture, and a possible anodal stimulation.

7. The device of claim 5, wherein in response to determining the difference between the values of the EA parameter in the first mode and the second mode exceeds the first threshold, the processor is further configured to:
determine whether the variability in the EA parameter for a different AVD in the first mode exceeds a predetermined third threshold; and
in response to determining the variability of the EA parameter for a different AVD in the first mode exceeds the third threshold, classify the stimulation as (c) possible anodal stimulation.

8. The device of claim 5, wherein in response to determining the difference between the values of the EA parameter in the first mode and the second mode exceeds the second threshold, the processor is further configured to:
determine whether the variability of the EA parameter for another different AVD in the first mode exceeds a given fourth threshold; and in response to determining the variability of the EA parameter for another different AVD in the first mode exceeds the fourth threshold, classify the stimulation as (b) a loss of a right ventricular capture or a left ventricular capture.

9. A method for an active implantable medical device that provides cardiac resynchronization by biventricular pacing, comprising:
receiving, from an endocardial acceleration sensor, an endocardial acceleration (EA) signal in a first mode, wherein only one of a left ventricle and a right ventricle are stimulated and a second mode, wherein both of a left ventricle and a right ventricle are stimulated,
extracting, from the EA signal, an EA parameter in each of the first mode and the second mode; and
comparing values of the EA parameter of the first mode to the values of the EA parameter of the second mode to distinguish between a plurality of operating conditions of the active implantable medical device; and
updating an operational parameter of the device based on the comparison of the values of the EA parameter in the first mode to the values of the EA parameter in the second mode.

10. The method of claim 9, wherein the plurality of operating conditions include (a) normal operation, (b) a loss of a right ventricular capture or a left ventricular capture, and (c) possible anodal stimulation.

11. The method of claim 9, wherein updating the operational parameter of the device based on the comparison of the values of the EA parameter in the first mode to the values of the EA parameter in the second mode comprises updating the operational parameter based on the determined operating condition.

12. The method of claim 9, wherein comparing the values of the EA parameters obtained in the first mode and the second mode comprises determining whether a difference between the values exceeds a first predetermined threshold.

13. The method of claim 12, wherein comparing the values of the EA parameters obtained in the first mode and the second mode comprises determining whether a difference between the values exceeds a second predetermined threshold.

14. The method of claim 13, further comprising:
applying an atrioventricular delay (AVD);
applying a right ventricular pacing at an end of the AVD in absence of a detected spontaneous ventricular event;
applying an interventricular delay (VVD) between times of stimulation of the left ventricle and the right ventricle; and
using the comparison of the values of the EA parameter in the first mode to the values of the EA parameter in the second mode to assess a variability of the EA parameter as a function of the AVD in the second mode to distinguish between the plurality of operating conditions.

15. The method of claim 14, further comprising:
in response to determining the difference between the values of the EA parameter in the first mode and the second mode exceeds the first threshold, determining whether the variability of the EA parameter for a different AVD in the first mode exceeds a predetermined third threshold; and
in response to determining the variability of the EA parameter for a different AVD in the first mode exceeds the third threshold, classifying the stimulation as (c) possible anodal stimulation.

16. The method of claim 14, further comprising:

in response to determining the difference between the values of the EA parameter in the first mode and the second mode exceeds the second threshold, determining whether the variability of the EA parameter for another different AVD in the first mode exceeds a given fourth threshold; and in response to determining the variability of the EA parameter for another different AVD in the first mode exceeds the fourth threshold, classifying the stimulation as (b) a loss of a right ventricular capture or a left ventricular capture.

17. An active implantable medical device that provides cardiac resynchronization by biventricular pacing, comprising:

a sensor configured to generate an endocardial acceleration (EA) signal in a first mode, wherein only one of a left ventricle and a right ventricle are stimulated, and a second mode, wherein both of a left ventricle and a right ventricle are stimulated; and processing electronics configured to:
receive the EA signal;
extract, from the EA signal, an EA parameter in each of the first mode and the second mode; and
compare values of the EA parameter of the first mode to the values of the EA parameter of the second mode to distinguish between a plurality of operating conditions of the active implantable medical device; and
update an operational parameter of the device based on the comparison of the values of the EA parameter in the first mode to the values of the EA parameter in the second mode.

18. The device of claim 17, wherein the plurality of operating conditions include (a) normal operation, (b) a loss of a right ventricular capture or a left ventricular capture, and (c) possible anodal stimulation.

19. The device of claim 17, wherein the processing electronics are further configured to:

apply an atrioventricular delay (AVD);
apply a right ventricular pacing at an end of the AVD in absence of a detected spontaneous ventricular event;
apply an interventricular delay (VVD) between times of stimulation of the left ventricle and the right ventricle; and
use the comparison of the values of the EA parameter in the first mode to the values of the EA parameter in the second mode to assess a variability of the EA parameter as a function of the AVD in the second mode to distinguish between the plurality of operating conditions.

20. The device of claim 19, further comprising a memory configured to:

test and store a plurality of different stimulation configurations with different VVD for a plurality of AVD.

* * * * *